(12) United States Patent
Geremakis et al.

(10) Patent No.: US 8,740,987 B2
(45) Date of Patent: Jun. 3, 2014

(54) TISSUE-DERIVED MESH FOR ORTHOPEDIC REGENERATION

(75) Inventors: Perry Geremakis, Manalapan, NJ (US); Jennifer Grasso, Cranford, NJ (US); David Knaack, Summit, NJ (US); Jo-Wen Lin, Tinton Falls, NJ (US); Lawrence Shimp, Morganville, NJ (US); Robert Waterman, New Hope, PA (US); John Winterbottom, Jackson, NJ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1226 days.

(21) Appl. No.: 11/018,853

(22) Filed: Dec. 20, 2004
(Under 37 CFR 1.47)

(65) Prior Publication Data
US 2005/0283255 A1  Dec. 22, 2005

Related U.S. Application Data (63) Continuation-in-part of application No. 10/433,523, filed on Jun. 4, 2003.

(60) Provisional application No. 60/531,485, filed on Dec. 19, 2003.

(51) Int. Cl.
*A61F 2/28* (2006.01)

(52) U.S. Cl.
USPC ............. 623/23.51; 606/151; 623/23.63; 623/13.17

(58) Field of Classification Search
USPC .......... 623/23.51, 23.63, 13.17, 13.18, 13.19, 623/23.57, 16.11; 606/76, 151
See application file for complete search history.

(56) References Cited

U.S. PATENT DOCUMENTS

| | | | | |
|---|---|---|---|---|
| 3,316,557 A | * | 5/1967 | Liebig | 623/1.38 |
| 3,625,811 A | * | 12/1971 | Okamura | 162/2 |
| 4,089,071 A | | 5/1978 | Kalnberz et al. | |
| 4,202,055 A | | 5/1980 | Reiner et al. | |
| 4,294,753 A | | 10/1981 | Urist | |
| 4,391,909 A | | 7/1983 | Lim | |
| 4,516,276 A | * | 5/1985 | Mittelmeier et al. | 623/16.11 |
| 4,713,076 A | | 12/1987 | Draenert | |
| 4,843,112 A | * | 6/1989 | Gerhart et al. | 523/114 |

(Continued)

FOREIGN PATENT DOCUMENTS

| | | | |
|---|---|---|---|
| EP | 0 306 018 A | 3/1989 | |
| EP | 0 485 986 A | 5/1992 | |

(Continued)

OTHER PUBLICATIONS

U.S. Appl. No. 12/050,856, von Eicken et al.

(Continued)

*Primary Examiner* — Paul Prebilic
(74) *Attorney, Agent, or Firm* — Sorell Lenna & Schmidt LLP (57) ABSTRACT

An implant including a substantially cohesive aggregate comprising bone-derived particles. Cohesiveness is maintained by a member of mechanical interlocking, engagement of adjacent bone-derived particles with one another through engagement with a binding agent, thermal bonding, chemical bonding, or a matrix material in which the bone-derived particles are retained. The aggregate is shaped as a one-dimensional or two-dimensional body.

11 Claims, 1 Drawing Sheet

(56) References Cited

U.S. PATENT DOCUMENTS

| | | | |
|---|---|---|---|
| 4,863,472 A * | 9/1989 | Tormala et al. | 623/23.58 |
| 4,877,864 A | 10/1989 | Wang et al. | |
| 4,880,610 A | 11/1989 | Constantz | |
| RE33,161 E | 2/1990 | Brown et al. | |
| 4,902,508 A | 2/1990 | Badylak et al. | |
| RE33,221 E | 5/1990 | Brown et al. | |
| 5,013,649 A | 5/1991 | Wang et al. | |
| 5,032,508 A * | 7/1991 | Naughton et al. | 435/32 |
| 5,034,059 A | 7/1991 | Constantz | |
| 5,047,031 A | 9/1991 | Constantz | |
| 5,053,049 A | 10/1991 | Campbell | |
| 5,053,212 A | 10/1991 | Constantz | |
| 5,061,286 A | 10/1991 | Lyle | |
| 5,073,373 A | 12/1991 | O'Leary et al. | |
| 5,084,050 A * | 1/1992 | Draenert | 606/77 |
| 5,092,887 A | 3/1992 | Gendler | |
| 5,106,748 A | 4/1992 | Wozney et al. | |
| 5,108,922 A | 4/1992 | Wang et al. | |
| 5,116,738 A | 5/1992 | Wang et al. | |
| 5,129,905 A | 7/1992 | Constantz | |
| 5,149,368 A | 9/1992 | Liu et al. | |
| 5,171,273 A * | 12/1992 | Silver et al. | 623/13.11 |
| 5,187,076 A | 2/1993 | Wozney et al. | |
| 5,243,038 A | 9/1993 | Ferrari et al. | |
| 5,262,166 A | 11/1993 | Liu et al. | |
| 5,263,984 A | 11/1993 | Li et al. | |
| 5,306,302 A * | 4/1994 | Bauer et al. | 623/23.63 |
| 5,314,476 A | 5/1994 | Prewett et al. | |
| 5,336,264 A | 8/1994 | Constanz et al. | |
| 5,338,772 A * | 8/1994 | Bauer et al. | 523/115 |
| 5,366,875 A | 11/1994 | Wozney et al. | |
| 5,378,469 A | 1/1995 | Kemp et al. | |
| 5,393,594 A | 2/1995 | Koyfman et al. | |
| 5,405,390 A | 4/1995 | O'Leary et al. | |
| 5,462,722 A | 10/1995 | Liu et al. | |
| 5,507,810 A | 4/1996 | Prewett et al. | |
| 5,507,813 A | 4/1996 | Dowd et al. | |
| 5,522,841 A | 6/1996 | Roby et al. | |
| 5,525,148 A | 6/1996 | Chow et al. | |
| 5,542,973 A | 8/1996 | Chow et al. | |
| 5,552,454 A | 9/1996 | Kretschmann et al. | |
| 5,587,507 A | 12/1996 | Kohn et al. | |
| 5,605,713 A | 2/1997 | Boltong et al. | |
| 5,607,269 A | 3/1997 | Dowd et al. | |
| 5,624,463 A | 4/1997 | Stone et al. | |
| 5,650,176 A | 7/1997 | Lee et al. | |
| 5,652,056 A * | 7/1997 | Pepin | 428/364 |
| 5,670,602 A | 9/1997 | Kohn et al. | |
| 5,705,181 A | 1/1998 | Cooper et al. | |
| 5,711,960 A | 1/1998 | Shikinami | |
| 5,717,006 A | 2/1998 | Daculsi et al. | |
| 5,814,476 A | 9/1998 | Kauffman et al. | |
| 5,837,752 A | 11/1998 | Shastri et al. | |
| 5,899,939 A | 5/1999 | Boyce et al. | |
| 5,948,386 A | 9/1999 | Katti et al. | |
| 5,962,427 A | 10/1999 | Goldstein et al. | |
| 5,989,894 A | 11/1999 | Lewis et al. | |
| 6,001,394 A | 12/1999 | Daculsi et al. | |
| 6,002,065 A | 12/1999 | Constantz et al. | |
| 6,048,964 A | 4/2000 | Lee et al. | |
| 6,090,998 A | 7/2000 | Grooms et al. | |
| 6,120,491 A | 9/2000 | Kohn et al. | |
| 6,123,727 A * | 9/2000 | Vacanti et al. | 424/422 |
| 6,123,731 A | 9/2000 | Boyce et al. | |
| 6,124,001 A | 9/2000 | Sugita et al. | |
| 6,132,871 A | 10/2000 | Andrews | |
| 6,183,498 B1 | 2/2001 | Devore et al. | |
| 6,206,957 B1 | 3/2001 | Driessens et al. | |
| 6,294,041 B1 | 9/2001 | Boyce et al. | |
| 6,294,187 B1 | 9/2001 | Boyce et al. | |
| 6,333,029 B1 * | 12/2001 | Vyakarnam et al. | 424/93.1 |
| 6,376,573 B1 | 4/2002 | White et al. | |
| 6,440,444 B2 | 8/2002 | Boyce et al. | |
| 6,441,073 B1 | 8/2002 | Tanaka et al. | |
| 6,478,825 B1 | 11/2002 | Winterbottom et al. | |
| 6,696,073 B2 * | 2/2004 | Boyce et al. | 424/422 |
| 6,843,807 B1 | 1/2005 | Boyce et al. | |
| 6,933,328 B2 | 8/2005 | Schacht | |
| 7,156,880 B2 * | 1/2007 | Evans et al. | 623/23.51 |
| 7,270,813 B2 | 9/2007 | Shimp et al. | |
| 7,291,345 B2 | 11/2007 | Winterbottom et al. | |
| 7,799,076 B2 * | 9/2010 | Sybert et al. | 623/13.17 |
| 2001/0008979 A1 * | 7/2001 | Bonutti | 623/13.17 |
| 2002/0035401 A1 | 3/2002 | Boyce et al. | |
| 2002/0107570 A1 * | 8/2002 | Sybert et al. | 623/13.17 |
| 2002/0128717 A1 | 9/2002 | Alfaro et al. | |
| 2003/0009235 A1 | 1/2003 | Manrique et al. | |
| 2003/0039676 A1 | 2/2003 | Boyce et al. | |
| 2003/0045942 A1 | 3/2003 | Lai et al. | |
| 2003/0065400 A1 * | 4/2003 | Beam et al. | 623/23.51 |
| 2003/0114552 A1 | 6/2003 | Schacht | |
| 2003/0130667 A1 | 7/2003 | Lin et al. | |
| 2003/0143258 A1 | 7/2003 | Knaack et al. | |
| 2003/0144743 A1 | 7/2003 | Edwards et al. | |
| 2003/0180344 A1 | 9/2003 | Wise et al. | |
| 2003/0194380 A1 * | 10/2003 | Szymaitis | 424/50 |
| 2003/0236573 A1 | 12/2003 | Evans et al. | |
| 2004/0024457 A1 | 2/2004 | Boyce et al. | |
| 2004/0034434 A1 | 2/2004 | Evans et al. | |
| 2004/0044409 A1 | 3/2004 | Alfaro et al. | |
| 2004/0048371 A1 | 3/2004 | Shimp et al. | |
| 2004/0064193 A1 | 4/2004 | Evans et al. | |
| 2004/0098129 A1 | 5/2004 | Lin et al. | |
| 2004/0138758 A1 | 7/2004 | Evans et al. | |
| 2004/0146543 A1 | 7/2004 | Shimp et al. | |
| 2004/0219058 A1 | 11/2004 | Shimp et al. | |
| 2004/0228898 A1 | 11/2004 | Ross et al. | |
| 2004/0243242 A1 | 12/2004 | Sybert et al. | |
| 2004/0249377 A1 | 12/2004 | Kaes et al. | |
| 2005/0008620 A1 | 1/2005 | Shimp et al. | |
| 2005/0008672 A1 | 1/2005 | Winterbottom et al. | |
| 2005/0027033 A1 | 2/2005 | Knaack et al. | |
| 2005/0031578 A1 | 2/2005 | Deslauriers et al. | |
| 2005/0038511 A1 | 2/2005 | Martz et al. | |
| 2005/0107880 A1 | 5/2005 | Shimp et al. | |
| 2005/0129726 A1 | 6/2005 | Liebschner | |
| 2005/0143740 A1 | 6/2005 | Morris et al. | |
| 2005/0148512 A1 * | 7/2005 | Hunter et al. | 514/12 |
| 2005/0209696 A1 | 9/2005 | Lin et al. | |
| 2005/0238683 A1 | 10/2005 | Adhikari et al. | |
| 2005/0240188 A1 | 10/2005 | Chow et al. | |
| 2005/0251146 A1 | 11/2005 | Martz et al. | |
| 2005/0251267 A1 | 11/2005 | Winterbottom et al. | |
| 2005/0281856 A1 | 12/2005 | McGlohorn et al. | |
| 2005/0283255 A1 * | 12/2005 | Geremakis et al. | 623/23.51 |
| 2006/0015184 A1 | 1/2006 | Winterbottom et al. | |
| 2006/0024656 A1 | 2/2006 | Morris et al. | |
| 2006/0030948 A1 | 2/2006 | Manrique et al. | |
| 2006/0095043 A1 | 5/2006 | Martz et al. | |
| 2006/0100498 A1 | 5/2006 | Boyce et al. | |
| 2006/0147545 A1 | 7/2006 | Scarborough et al. | |
| 2006/0149376 A1 | 7/2006 | Shimp et al. | |
| 2006/0216323 A1 | 9/2006 | Knaack et al. | |
| 2007/0073293 A1 | 3/2007 | Martz et al. | |
| 2007/0088437 A1 | 4/2007 | Betz et al. | |
| 2007/0098756 A1 | 5/2007 | Behnam et al. | |
| 2007/0110820 A1 | 5/2007 | Behnam et al. | |
| 2007/0154563 A1 | 7/2007 | Behnam et al. | |
| 2007/0168030 A1 | 7/2007 | Edwards et al. | |
| 2007/0178158 A1 | 8/2007 | Knaack et al. | |
| 2007/0191963 A1 | 8/2007 | Winterbottom et al. | |
| 2007/0231788 A1 | 10/2007 | Behnam et al. | |
| 2007/0233272 A1 | 10/2007 | Boyce et al. | |
| 2008/0009955 A1 | 1/2008 | Shimp et al. | |
| 2008/0063671 A1 | 3/2008 | Morris et al. | |
| 2008/0063684 A1 | 3/2008 | Winterbottom et al. | |
| 2008/0069852 A1 | 3/2008 | Shimp et al. | |
| 2008/0091270 A1 | 4/2008 | Miller et al. | |
| 2008/0145392 A1 | 6/2008 | Knaack et al. | |
| 2008/0154386 A1 | 6/2008 | Morris et al. | |
| 2008/0188945 A1 | 8/2008 | Boyce et al. | |
| 2008/0195202 A1 | 8/2008 | Lauritzen et al. | |

(56) References Cited

U.S. PATENT DOCUMENTS

| | | |
|---|---|---|
| 2008/0206299 A1 | 8/2008 | Shimp et al. |
| 2008/0260794 A1 | 10/2008 | Lauritzen et al. |
| 2008/0312695 A1 | 12/2008 | Sybert et al. |

FOREIGN PATENT DOCUMENTS

| | | |
|---|---|---|
| EP | 0 943 346 | 9/1999 |
| WO | WO 93/00432 | 1/1993 |
| WO | WO 94/26892 | 11/1994 |
| WO | WO 94/26893 | 11/1994 |
| WO | WO 98/19718 | 5/1998 |
| WO | WO 98/44965 | 10/1998 |
| WO | WO 99/21515 | 5/1999 |
| WO | WO 99/39757 | 8/1999 |
| WO | WO-99/39757 | 8/1999 |
| WO | WO-00/45747 | 8/2000 |
| WO | WO-00/50102 | 8/2000 |
| WO | WO-02/056800 | 7/2002 |
| WO | WO 02/056800 A2 | 7/2002 |
| WO | WO-03/030956 | 4/2003 |
| WO | WO-2004/014452 | 2/2004 |
| WO | WO-2004/032988 | 4/2004 |
| WO | WO-2004/053112 | 6/2004 |
| WO | WO-2004/069890 | 8/2004 |
| WO | WO-2005/062868 | 7/2005 |
| WO | WO-2005/065396 | 7/2005 |
| WO | WO2005062868 A2 * | 7/2005 |
| WO | WO-2005/072656 | 8/2005 |
| WO | WO-2005/074850 | 8/2005 |
| WO | WO-2005/107651 | 11/2005 |
| WO | WO-2007/084609 | 7/2007 |
| WO | WO-2007/084610 | 7/2007 |
| WO | WO-2007/084725 | 7/2007 |
| WO | WO-2008/086563 | 6/2009 |

OTHER PUBLICATIONS

U.S. Appl. No. 12/104,800, Avadhany et al.
U.S. Appl. No. 61/054,038.
U.S. Appl. No. 12/140,025.
U.S. Appl. No. 12/140,062.
U.S. Appl. No. 12/140,044.
U.S. Appl. No. 12/171,125.
U.S. Appl. No. 12/171,168.
U.S. Appl. No. 12/205,539.
U.S. Appl. No. 12/254,619.
U.S. Appl. No. 12/267,985.
U.S. Appl. No. 61/094,699.
U.S. Appl. No. 61/094,694.
U.S. Appl. No. 09/644,614.
U.S. Appl. No. 61/108,350.
U.S. Appl. No. 12/190,416.
Urist, "Bone: formation by autoinduction", *Science*, 150(698): 893-9, 1965, (Nov. 1965).

* cited by examiner

TISSUE-DERIVED MESH FOR ORTHOPEDIC REGENERATION

This application claims the priority of U.S. Provisional Application No. 60/531,485, filed Dec. 19, 2003 and is a continuation-in-part of U.S. patent application Ser. No. 10/433,523, filed Jun. 4, 2003 and having a priority date of Dec. 7, 2001.

FIELD OF THE INVENTION

This application pertains to tissue-derived implants for wound repair, and, more specifically, to one dimensional and two-dimensional tissue-derived materials for use in wound regeneration.

BACKGROUND OF THE INVENTION

Vertebrate bone is a composite material comprised of impure hydroxyapatite, collagen, and a variety of noncollagenous proteins, as well as embedded and adherent cells. Vertebrate bone can be processed into an implantable biomaterial, such as an allograft, for example, by removing the cells and leaving behind the extracellular matrix. The properties of the processed bone biomaterial depend upon the specific processes and treatments applied to it and may incorporate characteristics of other biomaterials with which it is combined. For example, bone-derived biomaterials may be processed into load-bearing mineralized grafts that support and integrate with the patient's bone, for example, as described in our commonly owned U.S. Pat. No. 6,123,731, or may alternatively be processed into soft, moldable or flowable demineralized bone biomaterials that have the ability to induce a cellular healing response, for example, as described in our commonly owned U.S. Pat. No. 5,814,476.

The use of bone grafts and bone substitute materials in orthopedic medicine is well known. While bone wounds can regenerate without the formation of scar tissue, fractures and other orthopedic injuries take a long time to heal, during which time the bone is unable to support physiologic loading unaided. Metal pins, screws, rods, plates and meshes are frequently required to replace the mechanical functions of injured bone. However, metal is significantly more stiff than bone. Use of metal implants may result in decreased bone density around the implant site due to stress shielding. Physiologic stresses and corrosion may cause metal implants to fracture. Unlike bone, which can heal small damage cracks through remodeling to prevent more extensive damage and failure, damaged metal implants can only be replaced or removed. The natural cellular healing and remodeling mechanisms of the body coordinate removal of bone and bone grafts by osteoclast cells and formation of bone by osteoblast cells. Ultimately, bone grafts are largely replaced by the recipient's own bone tissues.

The use of bone grafts is limited by the available shape and size of grafts. Bone grafts using cortical bone remodel slowly because of their limited porosity. Traditional bone substitute materials and bone chips are more quickly remodeled but cannot immediately provide mechanical support. In addition, while bone substitute materials and bone chips can be used to fill oddly shaped bone defects, such materials are not as well suited for wrapping or resurfacing bone. Thus, it is desirable to provide a tissue-derived implant that can be used to repair two-dimensional defects and whose remodeling rates are shorter than those of cortical bone.

A variety of implants having application as artificial bone, ligaments, tendons, cartilage, and the like, are also known. U.S. Pat. No. 4,089,071 describes a material for making bone endoprostheses featuring a laminated structure of net-like construction. U.S. Pat. No. 5,092,887 describes an elongated artificial ligament made from demineralized bone which is said to exhibit compliant elasticity and high longitudinal strength. U.S. Pat. No. 5,263,984 describes a prosthetic ligament made up of a quantity of substantially aligned, elongated filaments each of which is a biocompatible, resorbable fibril made, e.g., of collagen, elastin, reticulin, cellulose, algenic acid or chitosan. U.S. Pat. No. 5,711,960 describes an implant, useful inter alia, as a prosthetic or filling for a defective bone, which utilizes, as a base material, a biocompatible bulk structure of a three-dimensionally woven or knitted fabric of organic fibers whose surfaces have been biologically activated or inactivated. U.S. Pat. No. 6,090,998 describes a bone implant, useful for the repair or replacement of ligaments, tendons and joints, which includes at least one mineralized segment and at least one demineralized, flexible segment. Still, it would be useful to provide a one- or two-dimensional implant of interlocking fibrils for use in orthopedic and other tissue engineering applications.

DEFINITIONS

The term "architecture", as used herein, refers to the arrangement of fragments or particles in an aggregate. For example, the arrangement of particles in a mesh is different than that of particles in a braid. In some embodiments, a woven aggregate may have a more organized architecture than a pressed aggregate in which the particles are randomly oriented in at least two dimensions. Aggregates may also vary in porosity and pore size, shape, size, aspect ratios, etc.

As used herein, "bioactive agents" is used to refer to compounds or entities that alter, inhibit, activate, or otherwise affect biological or chemical events. For example, bioactive agents may include, but are not limited to, anti-AIDS substances, anti-cancer substances, antibiotics, immunosuppressants (e.g., cyclosporine), anti-viral agents, enzyme inhibitors, neurotoxins, opioids, hypnotics, anti-histamines, lubricants, tranquilizers, anti-convulsants, muscle relaxants and anti-Parkinson agents, anti-spasmodics and muscle contractants including channel blockers, miotics and anti-cholinergics, anti-glaucoma compounds, anti-parasite, anti-protozoal, and/or anti-fungal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, targeting agents, neurotransmitters, proteins, cell response modifiers, and vaccines. In a certain embodiments, the bioactive agent is a drug. In some embodiments, the bioactive agent is a growth factor, cytokine, extracellular matrix molecule or a fragment or derivative thereof, for example, a cell attachment sequence such as RGD.

A more complete listing of bioactive agents and specific drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", Edited by Susan Budavari et al., CRC Press, 1996, the United States Pharmacopeia-25/National Formular-20, published by the United States Pharmcopeial Convention, Inc., Rockville Md., 2001, and the "Pharmazeutische Wirkstoffe", edited by Von Keemann et al., Stuttgart/New York, 1987, all of which are incorporated herein by reference. Drugs for human use listed by the FDA under 21 C.F.R. §§330.5, 331 through 361, and 440 through 460 and drugs for veterinary use listed by the FDA under 21 C.F.R. §§500 through 589, all of which is incorporated herein by reference, are also considered acceptable for use in accordance with the present invention.

As used herein, "biodegradable", "bioerodable", or "resorbable" materials are materials that degrade under physiological conditions to form a product that can be metabolized or excreted without damage to organs. Biodegradable materials may be hydrolytically degradable, may require enzymatic action to fully degrade, or both. Other degradation mechanisms, e.g., thermal degradation due to body heat, are also envisioned. Biodegradable materials also include materials that are broken down within cells. Degradation may occur by hydrolysis, enzymatic degradation, phagocytosis, or other methods.

The term "biocompatible", as used herein, is intended to describe materials that, upon administration in vivo, do not induce undesirable long term effects.

The term "biomolecules", as used herein, refers to classes of molecules (e.g., proteins, amino acids, peptides, polynucleotides, nucleotides, carbohydrates, sugars, lipids, nucleoproteins, glycoproteins, lipoproteins, steroids, lipids, etc.) that are commonly found in cells and tissues, whether the molecules themselves are naturally-occurring or artificially created (e.g., by synthetic or recombinant methods). For example, biomolecules include, but are not limited to, enzymes, receptors, glycosaminoglycans, neurotransmitters, hormones, cytokines, cell response modifiers such as growth factors and chemotactic factors, antibodies, vaccines, haptens, toxins, interferons, ribozymes, anti-sense agents, plasmids, DNA, and RNA. Exemplary growth factors include but are not limited to bone morphogenic proteins (BMP's) and their active subunits and extracellular matrix components and active fragments thereof such as peptides containing RGD.

"Deorganified", as herein applied to matrices, particles, etc., refers to bone or cartilage matrices, particles, etc., that were subjected to a process that removes at least part of their original organic content.

"Nondemineralized", as herein applied to bone particles, refers to bone particles that have not been not subjected to a demineralization process (i.e., a procedure that totally or partially removes the original inorganic content of bone).

"One-dimensional": As used herein, the term "one-dimensional" indicates an object that is not significantly broader than it is thick and whose length is significantly longer than its thickness. Exemplary one dimensional objects may have the shape of strings, whiskers, threads, cables, braids, thin strips, coils, rods, strands, coiled strands, or fibers.

The term "osteoconductive", as used herein, refers to the ability of a substance or material to provide surfaces which are receptive to the growth of new host bone.

"Osteoinductive", as used herein, refers to the quality of being able to recruit cells from the host that have the potential to stimulate new bone formation. In one embodiment, osteoinductive materials are characterized by their ability to induce ectopic bone formation in muscle.

"Polynucleotide", "nucleic acid", or "oligonucleotide": The terms "polynucleotide," "nucleic acid," or "oligonucleotide" refer to a polymer of nucleotides. The terms "polynucleotide", "nucleic acid", and "oligonucleotide", may be used interchangeably. Typically, a polynucleotide comprises at least two nucleotides. DNAs and RNAs are polynucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thithymidine, inosine, pyrrolo-pyrimidine, 3-methyl adenosine, C5-propynylcytidine, C5-propynyluridine, C5-bromouridine, C5-fluorouridine, C5-iodouridine, C5 methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyriboses, arabinose, and hexose), or modified phosphate groups (e.g., phosphorothioates and 5'-N-phosphoramidite linkages). The polymer may also be a short strand of nucleic acids such as siRNA.

"Polypeptide", "peptide", or "protein": As used herein, a "polypeptide", "peptide", or "protein" includes a string of at least two amino acids linked together by peptide bonds. The terms "polypeptide, "peptide", and "protein", may be used interchangeably. Peptide may refer to an individual peptide or a collection of peptides. Inventive peptides preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, etc. In a preferred embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

The terms "polysaccharide" or "oligosaccharide", as used herein, refer to any polymer or oligomer of carbohydrate residues. The polymer or oligomer may consist of anywhere from two to hundreds to thousands of sugar units or more. "Oligosaccharide" generally refers to a relatively low molecular weight polymer. Starches are a species of polysaccharide and often indicate higher molecular weight polymers. Polysaccharides may be purified from natural sources such as plants or may be synthesized de novo in the laboratory. Polysaccharides isolated from natural sources may be modified chemically to change their chemical or physical properties (e.g., phosphorylated, cross-linked). Carbohydrate polymers or oligomers may include natural sugars (e.g., glucose, fructose, galactose, mannose, arabinose, ribose, and xylose) and/or modified sugars (e.g., 2'-fluororibose, 2'-deoxyribose, and hexose). Polysaccharides may also be either straight or branch-chained. They may contain both natural and/or unnatural carbohydrate residues. The linkage between the residues may be the typical ether linkage found in nature or may be a linkage only available to synthetic chemists. Examples of polysaccharides include cellulose, maltin, maltose, starch, modified starch, dextran, and fructose. Glycosaminoglycans are also considered polysaccharides. Sugar alcohol, as used herein, refers to any polyol such as sorbitol, mannitol, xylitol, galactitol, erythritol, inositol, ribitol, dulcitol, adonitol, arabitol, dithioerythritol, dithiothreitol, glycerol, isomalt, and hydrogenated starch hydrolysates.

"Small molecule": As used herein, the term "small molecule" is used to refer to molecules, whether naturally-occurring or artificially created (e.g., via chemical synthesis), that have a relatively low molecular weight. Typically, small molecules have a molecular weight of less than about 5000 g/mol. Preferred small molecules are biologically active in that they produce a local or systemic effect in animals, preferably mammals, more preferably humans. In certain preferred embodiments, the small molecule is a drug. Preferably, though not necessarily, the drug is one that has already been deemed safe and effective for use by the appropriate governmental agency or body.

As utilized herein, the phrase "superficially demineralized" as applied to bone particles refers to bone particles possessing at least about 90 weight percent of their original inorganic mineral content. The phrase "partially demineralized" as applied to the bone particles refers to bone particles possessing from about 8 to about 90 weight percent of their original inorganic mineral content, and the phrase "fully demineralized" as applied to the bone particles refers to bone particles possessing less than about 8, for example, less than about 1, weight percent of their original inorganic mineral content. The unmodified term "demineralized" as applied to the bone particles is intended to cover any one or combination of the foregoing types of demineralized bone particles.

"Thread": The term "thread" is used to describe a one-dimensional object without implying a particular aspect ratio or cross-sectional shape.

"Two-dimensional": As used herein, the term "two-dimensional" indicates an object that is significantly broader and longer than it is thick. For example, the object may have the shape of a ribbon, film, or mesh. The object need not be flat but may have significant curvature. For example, the object may have the shape of a portion of a sphere (e.g., a tent-like or umbrella like shape).

SUMMARY OF THE INVENTION

In one aspect, the invention is an implant including a substantially cohesive aggregate comprising bone-derived particles. Cohesiveness is maintained by a member of mechanical interlocking, engagement of adjacent bone-derived particles with one another through engagement with a binding agent, thermal bonding, chemical bonding, or a matrix material in which the bone-derived particles are retained. The aggregate is shaped as a one-dimensional or two-dimensional body.

The binding agent may be disposed within at least a portion of the individual bone-derived particles. The matrix material may be an extracellular matrix component, a non-bony tissue, a natural polymer, a synthetic, recombinant, or modified version of a natural polymer, or a synthetic polymer.

The aggregate may be laid, needle-punched, hooked, woven, rolled, pressed, bundled, braided, spun, plied, knitted, felted, drawn, spliced, cabled, extruded, knitted, cast, coated on a substrate, dipped, or dubbed on a substrate. The implant may include a plurality of aggregates, and the plurality of aggregates may differ in at least one of composition, size, shape, degree of mineralization, and architecture. For example, the aggregate may be a porous mesh suture, a ratcheting strap, a balloon, or a gauze. The gauze may be a woven mesh or a non-woven mesh. The aggregate may include a plurality of strands or a plurality of plies, wherein each ply has a plurality of strands.

The implant may further include one or more of trophic factors, adhesives, plasticizers, therapeutic agents, biostatic agents, biocidal agents, bioactive agents, biomolecules, or small molecules. Any of these agents may be deposited on a surface of the aggregate.

The implant may further include a solid additive, which may be a fiber or a particle. The additive may be a tissue-derived particle, a biocompatible ceramic, a natural polymer, a synthetic biodegradable polymer, a synthetic, recombinant, or modified version of a natural polymer, a metal, or a synthetic non-biodegradable polymer. The implant may further include a substrate on which the aggregate is coated.

The implant may further include cells for instance, for example, connective tissue cells, organ cells, muscle cells, nerve cells, or stem cells. In one embodiment these cells may be osteoblasts, osteoclasts, tenocytes, fibroblasts, chondrocytes, ligament cells, or mesenchymal stem cells.

The implant may be a composite including the aggregate and a second material. The second material may be a hydrogel, a ceramic, a metal, a natural polymer, a synthetic, recombinant, or modified version of a natural polymer, or a synthetic polymer.

In another aspect the invention is an implant including an assembled body comprising a plurality of one-dimensional substantially cohesive aggregates of bone-derived particles. Cohesiveness is maintained by one or more of mechanical interlocking, engagement of adjacent bone-derived particles with one another through engagement with a binding agent, thermal bonding, chemical bonding, or a matrix material in which the bone-derived particles are retained. The binding agent may be a metal oxide, a metal hydroxide, a metal salt of a inorganic or organic acid or a metal containing silica-based glass.

In another aspect the invention is a method of fabricating an implant. The method includes combining a quantity of bone-derived particles with an agent selected from a binding agent, a matrix material, a solvent and any combination of these to form a precursor material and forming a precursor material into an aggregate having a length to thickness ratio of at least two to one.

Combining may include contacting surfaces of the quantity of bone-derived particles with a solution of one or more binding agents in a polar solvent and the method further includes removing the polar solvent from the aggregate. A portion of the polar solvent may be removed before forming.

Forming may include one or more of pressing, compression molding, filament drawing, extruding, and solvent casting. The matrix material may be a polylactide, poly(L-lactide-co-DL-lactide), or tyrosine-based polycarbonate. Forming may include co-extruding the bone-derived particles and the matrix material or dubbing bone-derived particles on a strand of the matrix material. Forming may include one or more of laying, needle-punching, hooking, weaving, rolling, pressing, bundling, braiding, spinning, plying, knitting, felting, splicing, cabling, extruding, knitting, coating on a substrate, compression molding, molding, filament drawing, solvent casting, and dipping.

The method may further include repeating the method to produce a plurality of aggregates and forming the plurality into a multi-plied strand, braid, super braid, cable, super cable, woven mesh, non-woven mesh, or knitted mesh. The implant may be a one- or two-dimensional object, for example, a tape, ribbon, capillary network, film, fiber, mesh, sheet, rod, thread, strand, coiled strand, string, whisker, cable, braid, thin strip, mesh, or portion of a sphere.

BRIEF DESCRIPTION OF THE DRAWING

The invention is described with reference to the several figures of the drawing, in which, FIG. 1(A,B) is a schematic diagram of a method of producing bone particles for use with an embodiment of the invention.

DETAILED DESCRIPTION OF CERTAIN PREFERRED EMBODIMENTS

In one embodiment, an implant is fabricated from a solid aggregate comprising tissue-derived particles or fragments from, for example, allograft bone or small intestinal submucosa. The aggregate is shaped as a one dimensional body or a two dimensional body. The tissue-derived particles may be combined with other tissues, naturally-derived or engineered fibers, or synthetic biocompatible materials. The tissue-derived particles and other materials in the aggregate may be chemically bonded or interwoven with each other, or both, to form a continuous network. The implant may be fabricated as a porous film or fiber and used in applications where a one or two-dimensional material is desired. The shape exploits the mechanical and physiological properties of three-dimensional tissues such as bone while providing planar and thread-like implants to surgeons as an alternative to large blocks or runny pastes.

Materials

Figure 1A:
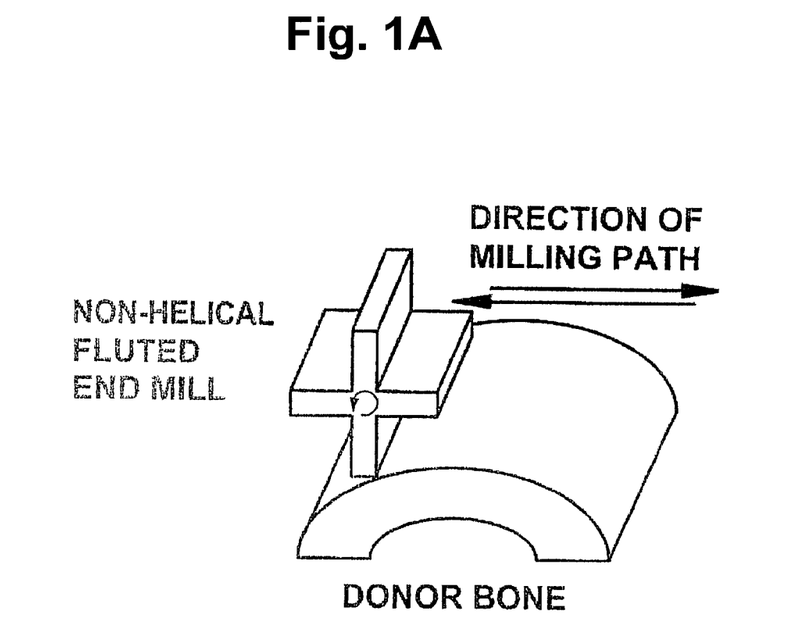
Figure 1B:
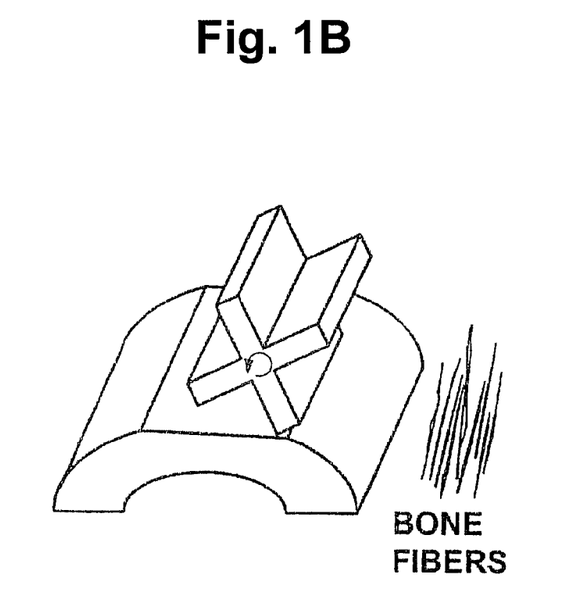

Bone particles may be obtained by milling or shaving sequential surfaces of an entire bone or relatively large section of bone. A non-helical, four fluted end mill may be used to produce fibers having the same orientation as the milled block. Such a mill has straight grooves, or flutes, similar to a reamer, rather than helical flutes resembling a drill bit. During the milling process, the bone may be oriented such that the natural growth pattern (along the long axis) of the piece being milled is along the long axis of the end mill of the milling machine. Multiple passes of the non-helical end mill over the bone results in bone fibers having a long axis parallel to that of the original bone (FIG. 1). As described herein, bone fibers are particles having at least one aspect ratio of 2:1 or greater. Bone fibers and other fibers have at least one dimension, such as length, that is longer than their width. In some embodiments, fibers may have at least one aspect ratio of at least 5:1, at least 10:1, at least 15:1, or even greater.

Elongated bone fibers may also be produced using the bone processing mill described in commonly assigned U.S. Pat. No. 5,607,269, the entire contents of which are incorporated herein by reference. Use of this bone mill results in the production of long, thin strips which quickly curl lengthwise to provide tube-like bone fibers. Elongated bone particles may be graded into different sizes to reduce or eliminate any less desirable size(s) of particles that may be present. In overall appearance, particles produced using this mill may be described as filaments, fibers, threads, slender or narrow strips, etc. In alternative embodiments, bone fibers and more evenly dimensioned particles may be produced by chipping, rolling, fracturing with liquid nitrogen, chiseling or planing, broaching, cutting, or splinting along the axis (e.g., as wood is split with a wedge).

Alternatively or in addition, an entire bone section or relatively large portion of bone may be cut longitudinally into elongated sections using a band saw or a diamond-bladed saw. Alternatively, the bone can be cut by making transverse cuts to prepare a bone section of the appropriate length, followed by longitudinal cuts using a band saw or a diamond cut saw. As stated above, elongated particles of bone can be further cut or machined into a variety of different shapes.

In one embodiment, bone particles are produced from fully mineralized human cortical bone. Bone particles for use in the aggregates according to the invention may also be obtained from cortical, cancellous, and/or corticocancellous bone which may be of autogenous, allogenic and/or xenogeneic origin and may or may not contain cells and/or cellular components. Porcine and bovine bone are particularly advantageous types of xenogeneic bone tissue that may be used individually or in combination as sources for the bone particles. Bone particles for use in the composites of the invention may have a length greater than 0.5 mm, for example, greater than 1 mm, greater than 2 mm, greater than 10 mm, greater than 100 mm, or greater than 200 mm, a thickness between 0.05 and 2 mm, for example, between 0.2 and 1 mm, and a width between 1 and 20 mm, for example, between 2 and 5 mm. Bone particles may be evenly dimensioned (e.g., having aspect ratios between 1:1 and 2:1) or may be elongated. In some embodiments, bone derived particles may possess a median length to median thickness ratio of at least 2:1, at least 5:1, at least 10:1, at least 15:1, or even greater, for example, at least 20:1, 30:1, 40:1, 50:1, or 100:1. In some embodiments, the ratio of length to thickness may range up to 500:1 or more. In addition, bone particles may have a median length to median width ratio of at least 2:1, at least 5:1, at least 10:1, at least 15:1, or even greater, for example, at least 20:1, 30:1, 40:1, 50:1, 100:1, or 200:1.

The bone particles may be sieved into different diameter sizes to eliminate any less desirable size(s) of fibers or more evenly dimensioned particles that may be present. In one embodiment, fibers collected from the milling machine may be lyophilized and manually sieved into a range of 300 µm to 500 µm in a particular cross-sectional dimension. One skilled in the art will recognize that the sieving method will determine what aspect must fall within 300-500 µm. Fiber length is independent of cross-sectional dimension and may be modified by adjusting the bit engagement length, the length of the bit in contact with the bone during the milling operation. Fibers may be an inch long or greater and may be as short as desired, depending on the desired aspect ratio. Fibers less than 50 µm long may increase the likelihood of inflammation depending on the tissues and how the implant degrades. Larger fibers may be further broken into smaller fibers by manually rolling them between the thumb and fingers and then sieved again to select the proper size fibers. Alternatively, fibers may be broken by pressing or rolling. The resulting fibers may have an aspect ratio of between 5:1 to 10:1. Broader or narrower fibers may be obtained by changing sieve grate sizes. Fibers with different widths and/or aspect ratios, for example, between 2:1 and 100:1, may be obtained by adjusting the milling parameters, including sweep speed, bit engagement, rpm, cut depth, etc.

Bone particles for use with the invention may optionally be partially or completely demineralized in order to reduce their inorganic mineral content. Demineralization methods remove the inorganic mineral component of bone, for example, by employing acid solutions. Such methods are well known in the art; see, for example, Reddi, et al., *Proc. Nat. Acad. Sci.*, 1972, 69:1601-1605, the contents of which are incorporated herein by reference. The strength of the acid solution, the shape of the bone particles and the duration of the demineralization treatment will determine the extent of demineralization. Reference in this regard may be made to Lewandrowski, et al., *J. Biomed. Mater. Res.*, 1996, 31: 365-372, the contents of which are also incorporated herein by reference.

In an exemplary demineralization procedure, the bone particles are subjected to a defatting/disinfecting step, followed by an acid demineralization step. An exemplary defatting/disinfectant solution is an aqueous solution of ethanol. Ordinarily, at least about 10 to about 40 percent by weight of water (i.e., about 60 to about 90 weight percent of defatting agent such as alcohol) is present in the defatting/disinfecting solution to optimize lipid removal and disinfection and processing time. An exemplary concentration range of the defatting solution is from about 60 to about 85 weight percent alcohol, for example, about 70 weight percent alcohol. Following defatting, the bone particles are immersed in acid over time to effect their demineralization. The acid also disinfects the bone by killing viruses, vegetative microorganisms, and spores. Acids that may be employed in this step include inorganic acids such as hydrochloric acid and organic acids such as peracetic acid. Alternative acids are well known to those skilled in the art. After acid treatment, the demineralized bone particles are rinsed with sterile water to remove residual amounts of acid and raise the pH. The bone particles may be dried, for example, by lyophilization, before being incorporated into the composite. The bone particles may be stored under aseptic conditions until they are used or sterilized using known methods shortly before incorporation into the composite. Additional demineralization methods are well known to those skilled in the art, for example, the method cited in Urist M R, A morphogenetic matrix for differentiation of bone tissue, *Calcif Tissue Res*. 1970; Suppl:98-101 and Urist M R, Bone: formation by autoinduction, *Science*. 1965 Nov. 12; 150(698):893-9, the contents of both of which are incorporated herein by reference.

In an alternative embodiment, surfaces of bone particles may be lightly demineralized according to the procedures in our commonly owned U.S. patent application Ser. No. 10/285,715, published as U.S. Patent Publication No. 20030144743. Even minimal demineralization, for example, of less than 5% removal of the inorganic phase, exposes reactive surface groups such as hydroxyl and amine. Demineralization may be so minimal, for example, less than 1%, that the removal of the calcium phosphate phase is almost undetectable. Rather, the enhanced surface concentration of reactive groups defines the extent of demineralization. This may be measured, for example, by titrating the reactive groups. In one embodiment, in a polymerization reaction that utilizes the exposed allograft surfaces to initiate a reaction, the amount of unreacted monomer remaining may be used to estimate reactivity of the surfaces. Surface reactivity may be assessed by a surrogate mechanical test, such as a peel test of a treated coupon of bone adhering to a polymer. Alternatively or in addition, a portion of the surface of the bone particles may be so demineralized.

In one embodiment, when the bone particles are of such size as to be relatively inflexible prior to demineralization, they may be demineralized to the point where they are flexible and capable of being worked, e.g., woven, braided, spun, etc. When bone elements are of such dimensions that they are relatively flexible prior to demineralization, a lesser degree of demineralization may be appropriate. The extent of demineralization necessary to obtain a bone element that is workable can be readily determined by one skilled in the art employing routine experimentation and will depend partially on how the aggregate is assembled. In some embodiments, the aggregates may be produced from non-demineralized bone particles.

Alternatively, the surface of a bone or ceramic particle may be treated to modify its surface composition. For example, nondemineralized bone particles may be rinsed with dilute phosphoric acid (e.g., for 1 to 15 minutes in a 5-50% solution by volume). Phosphoric acid reacts with the mineral component of the bone and coats the particles with a relatively purified phase of calcium phosphate, for example, dicalcium phosphate dihydrate. Treated surfaces may further be reacted with silane coupling agents as described above. Alternatively or in addition, bone or ceramic particles may be dried. For example, particles may be lyophilized for varying lengths of time, e.g., about 8 hours, about 12 hours, about 16 hours, about 20 hours, or a day or longer. Moisture may be removed by heating the particles to an elevated temperature, for example, 60° C., 70° C., 80° C., or 90° C., with or without a dessicant.

Mixtures or combinations of one or more of the above types of bone particles can be used to produce aggregates according to the invention. For example, one or more of the foregoing types of demineralized bone particles can be employed in combination with nondemineralized bone particles, i.e., bone particles that have not been subjected to a demineralization process. The combination of differently processed bone particles may be optimized to provide a particular mechanical property, such as mechanical strength or elastic modulus, or to modify the rate of degradation or the mechanism of tissue formation. For example, ceramic or nondemineralized bone particles may increase the strength and stiffness of an aggregate, while demineralized bone particles are more osteoinductive than mineralized tissue.

Non-bony tissues suitable for use with the invention include connective tissue such as tendon, ligament, cartilage, endodermis, small intestine submucosa, and muscle. Tendon tissue useful for fabricating the aggregate includes, but is not limited to, fascia lata, semitendinosus, achilles tendon and patella tendon tissue. Ligament tissue may include an entire excised ligament or elongated section thereof. Small intestine submucosa tissue can be obtained and processed as described in U.S. Pat. No. 4,902,508, the contents of which are incorporated by reference herein. In summary, intestinal tissue is abraded to remove the outer layers, including both the tunica serosa and the tunica muscularis and the inner layers, including at least the luminal portion of the tunica mucosa. The resulting material is a whitish, translucent tube of tissue approximately 0.1 mm thick, typically consisting of the tunica submucosa with the attached lamina muscularis mucosa and stratum compactum. The tissue may be rinsed in 10% neomycin sulfate before use.

Non-bony tissues may be obtained from autogeneic, allogeneic or xenogeneic sources. The tissues may be excised and cut into a plurality of elongated fragments or particles employing methods known in the art. Reduction of the antigenicity of allogeneic and xenogeneic tissue can be achieved by treating the tissues with various chemical agents, e.g., extraction agents such as monoglycerides, diglycerides, triglycerides, dimethyl formamide, etc., as described, e.g., in U.S. Pat. No. 5,507,810, the contents of which are incorporated by reference herein.

The implant may also be fabricated from other extracellular matrix components, including but not limited to collagen, laminin, elastin, proteoglycans, reticulin, fibronectin, vitronectin, glycosaminoglycans, and other basement membrane components. Various types of collagen (e.g., collagen Type I, collagen Type II, collagen Type IV) are suitable for use with the invention. Collagens may be used in fiber, gel, or other forms. Sources for extracellular matrix components include, but are not limited to, skin, tendon, intestine and dura mater obtained from animals, transgenic animals and humans. Extracellular matrix components are also commercially available, for example, from Becton Dickenson. Collagenous tissue can also be obtained by genetically engineering microorganisms to express collagen as described, e.g., in U.S. Pat. No. 5,243,038, the entire contents of which are incorporated herein by reference. Procedures for obtaining and purifying collagen are well known in the art and typically involve acid or enzyme extraction as described, e.g., in U.S. Pat. No. 5,263,984, the contents of which are incorporated by reference herein. The purified collagen is then subjected to further processing to obtain collagen fibers or collagen threads, which can optionally be treated with crosslinking agents, e.g., glutaraldehyde, to improve their strength and/or with various medically/surgically useful substances as described above. The collagen threads can be arranged to form various structures, such as a woven or non-woven fabric, bundle or braid, etc. by various techniques known in the art as described, e.g., in U.S. Pat. Nos. 5,171,273 and 5,378,469, each incorporated herein by reference. For example, U.S. Pat. No. 5,171,273 describes the preparation of high-strength collagen fibers by dissolving Type I collagen in dilute hydrochloric acid and extruding the solution into a specific fiber formation buffer to reconstitute the collagen fibers. The reconstituted collagen fibers may be subsequently crosslinked with glutaraldehyde or other chemical agents and treatments.

Other natural polymers that may be exploited for use with the invention include cellulose, alginic acid, chitosan, cotton, catgut, starches, collagen-GAG, oxidized cellulose, fibrin, and silk. Synthetic and recombinant versions or modified versions of natural polymers may also be used. Exemplary synthetic ECM analogs include silk-elastin polymers produced by Protein Polymer Technologies (San Diego, Calif.) and BioSteel™, a recombinant spider silk produced by Nexia Biotechnologies (Vaudrevil-Dorion, QC, Canada). Recominant fibers may be obtained from microorganisms, for example, genetically engineered microorganisms such as yeast and bacteria and genetically engineered eucaryotic cell cultures such as Chinese hamster ovary cell lines, HeLa cells, etc. For example, U.S. Pat. Nos. 5,243,038 and 5,989,894, each of which is incorporated herein by reference, describes the expression of spider silk protein, collagen proteins, keratins, etc., using genetically engineered microorganisms and eucaryotic cell lines.

Natural and recombinant fibers may be modified in a variety of ways before being incorporated into an aggregate. For example, fibrous tissues may be frayed to expose protein chains and increase the surface area of the tissue. Rinsing fibrous tissue or partially demineralized bone particles in an alkaline solution, or simply partially demineralizing bone particles, will fray fibrous proteins within the tissue. For example, bone fibers may be suspended in aqueous solution at a pH of about 10 for about 8 hours, after which the solution is neutralized. One skilled in the art will recognize that this time period may be increased or decreased to adjust the extent of fraying. Agitation, for example, in an ultrasonic bath, may assist in fraying and/or separating collagen fibers, as well as improving penetration of acidic, basic, or other fluids, especially for bony tissues. Alternatively or in addition, bone or inorganic calcium phosphate particles (see below) may be mechanically stirred or shaken, with or without the addition of abrasives.

Polymers and fibrous tissues, especially those containing collagen, such as bone and tendon, may be cross-linked before incorporation into an aggregate. A variety of cross-linking techniques suitable for medical applications are well known in the art. For example, compounds like 1-ethyl-3-(3-dimethylaminopropyl) carbodiimide hydrochloride, either alone or in combination with N-hydroxysuccinimide (NHS) will crosslink collagen at physiologic or slightly acidic pH (e.g., in pH 5.4 MES buffer). Acyl azides and genipin, a naturally occurring bicyclic compound including both carboxylate and hydroxyl groups, may also be used to cross-link collagen chains (see Simmons, et al, "Evaluation of collagen cross-linking techniques for the stabilization of tissue matrices," *Biotechnol. Appl. Biochem.*, 1993, 17:23-29; PCT Publication WO98/19718, the contents of both of which are incorporated herein by reference). Alternatively, hydroxymethyl phosphine groups on collagen may be reacted with the primary and secondary amines on neighboring chains (see U.S. Pat. No. 5,948,386, the entire contents of which are incorporated herein by reference). Standard cross-linking agents such as mono- and dialdehydes, polyepoxy compounds, tanning agents including polyvalent metallic oxides, organic tannins, and other plant derived phenolic oxides, chemicals for esterification or carboxyl groups followed by reaction with hydrazide to form activated acyl azide groups, dicyclohexyl carbodiimide and its derivatives and other heterobifunctional crosslinking agents, hexamethylene diisocyanate, ionizing radiation, and sugars may also be used to cross-link fibrous tissues and polymers. The tissue is then washed to remove all leachable traces of the material. Enzymatic cross-linking agents may also be used. One skilled in the art will easily be able to determine the optimal concentrations of cross-linking agents and incubation times for the desired degree of cross-linking.

Synthetic polymers may also be used in the aggregates described herein. Exemplary polymers include, but are not limited to, tyrosine based polycarbonates and polyarylates such as those described by U.S. Pat. Nos. 5,587,507, 5,670, 602, and 6,120,491, such as poly(desaminotyrosyltyrosine (ethyl ester) carbonate) (PolyDTE carbonate), poly(desaminotyrosyltyrosine carbonate) (PolyDT carbonate), and co-polymers of these in ratios of, e.g., 25:75, 40:60, 60:40, or 75:25. One skilled in the art will recognize that other osteoconductive polymers may also be used with the invention. Additional biodegradable polymers include polylactides, polycaprolactones, polyglycolides, lactide-glycolide copolymers having ratios of, e.g., 85:15, 40:60, 30:70, 25:75, or 20:80, poly(L-lactide-co-D,L-lactide), polyglyconate, polyhydroxybutyrate, polyhydroxyvalerate, polyhydroxybutyrate/valerate copolymers, polyurethanes including glucose-based polyurethanes, poly(arylates), poly(anhydrides), poly (hydroxy acids), polyesters, poly(ortho esters), poly(alkylene oxides), poly(propylene glycol-co fumaric acid), poly(propylene fumerates), polycarbonates, polyoxamers, polyamino acids, polyacetals, poly(dioxanones), poly(epsilon caprolactone-co-p-dioxanone), poly(vinyl pyrrolidone), biodegradable polycyanoacrylates, and polysaccharides. Additional polymers include bioabsorbable block copolymers made of hard phase forming monomers, e.g., glycolide and lactide, and soft phase monomers, e.g., 1,4 dioxane-2-one and caprolactone, as described, e.g., in U.S. Pat. No. 5,522,841, incorporated herein by reference.

Non-biodegradable polymers may also be employed for use with the invention. Exemplary non-biodegradable, yet biocompatible polymers include polystyrene, polysulfones, polyesters, polyureas, poly(vinyl alcohol), polyamides, poly (tetrafluoroethylene), and expanded polytetrafluroethylene (ePTFE), poly(ethylene vinyl acetate), polypropylene, polyacrylate, non-biodegradable polycyanoacrylates, non-biodegradable polyurethanes, mixtures and copolymers of poly (ethyl methacrylate) with tetrahydrofurfuryl methacrylate, polymethacrylate, poly(methyl methacrylate), poly(vinyl chlorides), polyethylene, including ultra high molecular weight polyethylene (UHMWPE), polypyrrole, polyanilines, polythiophene, poly(ethylene oxide), poly(ethylene oxide co-butylene terephthalate), poly ether-ether ketones (PEEK), and polyetherketoneketones (PEKK). Co-polymers, mixtures, and adducts of any of these biodegradable and non-biodegradable polymers may also be employed for use with the invention.

Inorganic materials may also be combined with bone to form aggregates. For example, non-bony calcium phosphate materials may also be exploited for use with the invention. Exemplary inorganic ceramics for use with the invention include calcium carbonate, calcium sulfate, calcium phosphosilicate, sodium phosphate, calcium aluminate, calcium phosphate, hydroxyapatite, α-tricalcium phosphate, dicalcium phosphate, β-tricalcium phosphate, tetracalcium phosphate, amorphous calcium phosphate, octacalcium phosphate, and BIOGLASS™, a calcium phosphate silica glass available from U.S. Biomaterials Corporation. Substituted CaP phases are also contemplated for use with the invention, including but not limited to fluorapatite, chlorapatite, Mg-substituted tricalcium phosphate, and carbonate hydroxyapatite. Additional calcium phosphate phases suitable for use with the invention include those disclosed in U.S. Pat. Nos. RE 33,161 and RE 33,221 to Brown et al.; U.S. Pat. Nos. 4,880,610; 5,034,059; 5,047,031; 5,053,212; 5,129,905; 5,336,264; and 6,002,065 to Constantz et al.; U.S. Pat. Nos. 5,149,368; 5,262,166 and 5,462,722 to Liu et al.; U.S. Pat. Nos. 5,525,148 and 5,542,973 to Chow et al., U.S. Pat. Nos. 5,717,006 and 6,001,394 to Daculsi et al., U.S. Pat. No. 5,605,713 to Boltong et al., U.S. Pat. No. 5,650,176 to Lee et al., and U.S. Pat. No. 6,206,957 to Driessens et al, and biologically-derived or biomimetic materials such as those identified in Lowenstam H A, Weiner S, *On Biomineralization*, Oxford University Press, 234 pp. 1989, incorporated herein by reference. Non-calcium ceramics such as alumina or zirconia are also appropriate for use according to the teachings herein.

Alternatively or in addition, metallic materials may also be employed in aggregates. Exemplary materials include titanium and titanium alloy fibers such as NiTi (shape memory materials) and Ti-6Al-4V. Additional metallic materials include biocompatible steels and cobalt-chromium-molybdenum alloys.

The dimensions of the various natural, recombinant, and synthetic materials making up an aggregate may vary widely depending on the dimensions of the site to which the final implant is to be affixed. In one embodiment, these dimensions may range from about 1 cm to about 1 meter in length, for example, from about 3 cm to about 8 cm in length, from about 0.5 mm to about 30 mm in thickness, for example, from about 2 mm to about 10 mm in thickness, and from about 0.05 mm to about 150 mm in width, for example, from about 2 mm to about 10 mm in width.

Production of an Aggregate

A wide variety of techniques may be used to fabricate the aggregates according to the invention. In one embodiment, elongated bone-derived particles or fragments of small intestinal submucosa (for example, approximately 6) are combined longitudinally into three small bundles, each having, for example, from about 1 to about 3 tissue particles. The three bundles are then braided. Various methods of braiding and types of braids any of which may be useful in producing the material of the invention herein are also described, e.g., by Shaw, KNOTS—Useful & Ornamental, Bonanza Books, New York (1983), incorporated herein by reference. The ends of the braided tissue-derived particles may then be glued together using a fixation agent to prevent their unraveling, or they may be held together with a biocompatible polymer or metal band.

In an alternative embodiment, bone-derived particles are combined with a solvent to form a precursor. Since the solvent will usually be removed, it does not have to be non-toxic; however, a biocompatible solvent is preferred. Exemplary solvents include water, lower alkanols, ketones, and ethers and mixtures of any of these. The precursor may then extruded at an appropriate temperature and pressure to create a thread that is then fashioned into a final implant shape. Threads may also be produced by spinning, drawing, rolling, solvent-extruding, cutting or laser cutting from a sheet or bar stock. The precursor may alternatively be cast or molded into a solid sheet or bar stock and then cut into thin threads. These may be used immediately or woven into a mesh. Alternatively or in addition, they may be spliced, wrapped, plied, cabled, braided, woven, or some combination of these. The precursor may be shaped by thermal or chemical bonding, or both. In one embodiment, a portion of the solvent is removed from the precursor before extrusion.

Alternatively or in addition, the precursor material may be cast as a slurry, extruded, or molded. A variety of materials processing methods will be well known to those skilled in the art. For example, the precursor material may be solvent cast using a press such as a Carver press to spread the precursor into a film. Solvent evaporation will yield a porous film. Alternatively, the precursor material may be compression molded into a film. The mesh size or porosity of the film will depend on the thickness of the film and the viscosity of the precursor and can be easily manipulated by one skilled in the art. Where elongated particles are used in an extruded aggregate, they will tend to be aligned roughly parallel to one another.

In an alternative embodiment employing a precursor of bone particles and a solvent, a binding agent is included in the precursor either before or after forming the aggregate. For example, the bone particles and binding agent solution may be combined in a slurry or formed into a green body. The precursor, including the binding agent, may be cast, molded, extruded, or otherwise processed as discussed above. In one embodiment, a mixture of the bone particles and a solvent is extruded and the resulting thread passed through a bath to coat the thread with the binding agent.

The binding agent links adjacent bone particles either directly or by forming bridge-like structures between them. In one embodiment, inorganic binding agents include a metal oxide, metal hydroxide, metal salt of an inorganic or organic acid, or a metal containing silica-based glass. The metal may be endogenous (e.g., bone derived calcium) or exogenous. The metal may be divalent, for example, an alkaline earth metal, e.g., calcium. A variety of appropriate solvents and binding agents are disclosed in our commonly owned U.S. Pat. No. 6,478,825, the entire contents of which are incorporated herein by reference. In one embodiment, the binding agent is at least slightly soluble in a polar solvent to promote precipitation. Since the solvent will usually be removed to precipitate the binding agent on the surfaces of the bone derived elements, the solvent does not have to be non-toxic; however, a biocompatible solvent is preferred. Exemplary solvents include water, lower alkanols, ketones, and ethers and mixtures of any of these.

A precursor according to any of the above embodiments may also be deposited on a substrate. For example, fibers of a biocompatible polymer may be coated in the precursor material, e.g., by dipping. After the solvent evaporates, the polymer fiber may be used in the same manner as tissue fibers or aggregates. For example, it may be woven or cabled. If the precursor is of sufficiently low viscosity, it may be used to coat surfaces of a three-dimensional substrate, such as a sponge or tube. Any shape substrate may be coated with a precursor according to the invention, including a bone, sponge, cone, portion of cone, tube, particle, rod, sphere, strand, coiled strand, capillary network, film, fiber, mesh, sheet, threaded cylinder, rod, hinge, rivet, anchor, spheroid, ellipsoid, oblate spheroid, prolate ellipsoid, or hyperbolic paraboloid. Coated polymeric implants may exhibit increased mechanical stability. For example, a porous or solid polymer sheet may be coated with the implant of the invention to add mechanical stability, slow resorption, and attract bone cells. These implants may also be used to create porous networks in bony wound sites, providing a migration path for cells to the interior of the wound site and allowing the entire site to be remodeled at the same time. In contrast, a block of bone is primarily remodeled from the surface inwards. In another embodiment, a polymer sheet is patterned with the precursor. For example, a polymer sheet, for example, a mesh or film, may be rolled with a patterned roller that deposits the precursor. Alternatively, the polymer sheet may be pressed against a patterned plate or stamp that deposits the precursor in a predetermined pattern. In an additional embodiment, the precursor may be cast on bulk substrates such as prostheses to promote integration of the implant in the body.

In an alternative embodiment, a thread of a biocompatible natural or synthetic material, for example, polylactide or collagen, is coated with tissue-derived elements by dubbing. For example, a polymer fiber is coated with an adhesive, for example, lecithin, and bone particles or other osteoconductive or osteoinductive fibrils allowed to adhere to the thread. The thread is then twisted on itself or with a second or a plurality of similarly treated threads. Alternatively or in addition, the threads may be braided. The adhesive may be a lipid that is waxy at room temperature, for example, a di- or triglyceride that is solid at room temperature. Alternatively or in addition, the adhesive may be a phosphocholine. In some embodiments, the adhesive is a material that binds both the thread and the material that is used to coat the thread (e.g., bone particles) but that does not degrade either. Non-aqueous adhesives may improve the stability of the final aggregate as compared to aqueous adhesives. One skilled in the art will recognize that where bone particles are combined with an elongated or sheet-like substrate, the bone particles themselves need not be elongated. In addition, the use of a coated thread can combine the flexibility of the polymer with the osteoconductivity of mineralized bone. Longer pieces of mineralized bone might be too stiff to manipulate in the same manner as the coated thread.

Coating and dubbing are not the only methods in which a substrate material may be used to support tissue particles in a cohesive aggregate. For example, a sheet of a biocompatible polymer may be needle-punched or hooked with fibers produced according to the invention. Alternatively, an aggregate in the form of a pressed sheet or mesh may be needle-punched or hooked with fibers to modify the texture of the implant. Alternatively, a natural, recombinant, or synthetic polymer may be co-extruded with tissue particles. For example, a polymer and tissue particles may be combined in a hopper and extruded using known polymer fabrication techniques. Where elongated tissue particles, especially bone particles, are used, they will tend to be relatively aligned with the axis of the extruded polymer. The stiffness and other mechanical properties of the extruded fiber may be controlled by adjusting particle size, the degree of demineralization (for bone) and the ratios and compositions of the components. Aggregates in the form of polymer-tissue composites may be extruded in practically any shape, including both one and two dimensional shapes. These shapes need not be strictly round or sheet like—the cross-section of extruded polymer-tissue aggregates may have virtually any geometric shape, including triangles and other polygons and shapes with concave or convex sides.

Aggregates of both fibers and more evenly dimensioned tissue fragments may be formed utilizing well known techniques, e.g., braiding, plying, knitting, weaving, felting, that are applied to processing natural fibers, e.g., cotton, silk, etc., and synthetic fibers made from synthetic bioabsorbable polymers, e.g., poly(glycolide) and poly(lactic acid), nylon, cellulose acetate, etc. See, e.g., Mohamed, American Scientist, 78: 530-541 (1990). For example, aforementioned U.S. Pat. No. 5,378,469 describes the braiding of crosslinked and non-crosslinked collagen threads using a harness braiding machine (New England Butt Co., Providence, R.I.). Specifically, collagen thread is wound onto cylindrical stainless steel spools. The spools are then mounted onto the braiding carousel, and the collagen thread is then assembled in accordance with the instructions provided with the braiding machine. In one particular run, a braid was formed of four collagen threads, which consisted of two threads of uncrosslinked collagen and two threads of crosslinked collagen. One skilled in the art will recognize that these techniques may be applied to the other fibrous materials described herein.

Fibers and more evenly dimensioned particles may also be plied into yarns using the same methods and same machinery known to those skilled in the art in plying threads made out of other material, e.g., cotton, polyester, etc. For example, U.S. Pat. No. 5,378,469 describes the production of a 60 ply yarn from noncrosslinked collagen threads. Four collagen threads were twisted together. Three of the resultant 4-ply strands were then twisted together in the opposite direction, and then 5 of the resultant 12 ply strands were twisted in the opposite direction.

Elongated aggregates, including multistranded aggregates, e.g., braids, plied yarns, cables, etc., may be knitted into tubular or flat fabrics by using techniques known to those skilled in the art of producing fabrics manufactured from other types of threads. Various biologically active substances can be incorporated in, or associated with, the braided, knitted, or woven materials. Particles and fibers and aggregates of these (including multistranded aggregates) may alternatively or additionally be assembled into an aggregate by non-woven methods such as laying, needle-punching, and hooking (as for a rug). For example, a thread may be attached to another thread or a pressed film.

Regardless of the assembly method, the aggregate shape, mesh size, cable thickness, and other structural characteristics, e.g., architecture, may be customized for the desired application. For example, where a two dimensional aggregate is used to retain a thixotropic material within a gap, a tight weave is preferred to prevent leakage. If it is desirable to permit cells or fluids to migrate through the mesh, the pore size should be optimized for the viscosity and surface tension of the fluid or the size of the cells. For example, pore sizes on the order of 100-200 µm may be preferred if cells are to migrate through the mesh. Mesh size may be controlled by physically weaving strands of the tissue material or of the aggregate or by controlling the ratio of solvent to solids in a precursor material.

One-dimensional implants may be produced in a variety of widths and tensile strengths. Thicker threads of the implants will have lower tensile strengths than cables of several thinner threads and will be more quickly resorbed. Individual cables may be cabled together to form an even stronger supercable. Such multi-level structures mimic those found in many tissues of the body, including tendon and muscle. Cabled threads will also retain more of their original mechanical strength as they are remodeled.

Particles derived from bone and small intestinal mucosa may also be combined with other structural materials to form aggregates. For example, tissue-derived particles may be combined with natural or synthetic fibers and/or other materials to provide an elongated thread or cable. For example, relatively short bone elements can be combined with other materials in a known manner, e.g., to form a spun yarn, which can then be woven to form the implant of the invention. Thus, the short bone elements can be combined with demineralized bone elements of greater length, other natural fibers, e.g., collagen fibers, polymeric fibers, ceramic or glass fibers, or biocompatible metal fibers of suitable length to produce a composite yarn which can may be manipulated as described above to form an aggregate.

In one embodiment, short particles may be combined with bioresorbable thermoplastic material that is formed into spun-bonded and/or non-woven fabrics. This embodiment is particularly useful for harder materials such as bone and ceramic particles. For example, after the bioresorbable thermoplastic material has been formed into a first web, the particles can be applied to the first web and then sandwiched with a second web to form a controlled elastic composite material. The methods of forming a composite material disclosed in U.S. Pat. Nos. 6,124,001 and 6,132,871 are incorporated by reference herein and are suitable for forming such an elastic composite.

Solid additives such as particles and fibers may also be combined with an aggregate to form an implant. The dimensions of such additives may be comparable to the dimensions of the bone-derived elements used to form the implant. The additives preferably should be biocompatible. Non-biodegradable additives will be encapsulated into new bone as the implant remodels or will be removed from the tissue site by cells as the implant is degraded. Exemplary additives include, without limitation, radio-opaque particles, for example, metal guidewires, and reinforcing materials that add shape or contour, e.g., a shaped metallic or polymer screen to which the precursor or implant is attached. K-wires may be used for fluoroscopic placement of the implant, and then removed before closure of the implant site. In addition, any of the materials that may be used to form the aggregate may also be combined with a fabricated aggregate to produce an implant.

In another embodiment, the aggregate may be combined with one or more additional materials to form a composite. For example, the aggregates of the invention may be used to add mechanical stability to a hydrogel. Ceramic implants incorporating the aggregates of the invention as fibers, meshes, or fragments will exhibit increased flexibility and tensile strength. Alternatively, fibers or sheets of other materials, such as PLA or poly(HEMA), may be co-woven or coiled with the aggregate. Synthetic polymers may be co-woven or cabled with the aggregate to increase the tensile strength of the material.

Biologically active substances may also be incorporated into aggregates or combined with aggregates and other materials in implants. For example, bioactive agents, small molecules, and biomolecules may all be retained on or in the aggregate material by covalent or non-covalent interactions. For example, proteins and polysaccharides will alter the surface properties of fibers and coils and the degradation rate of both fibers and meshes. Growth factors and trophic factors may recruit cells to the implant and promote specific metabolic activities. Exemplary growth factors include bone morphogenic proteins, osteoinductive factor, fibronectin, transforming growth factor-beta, endothelial cell growth factor, cementum attachment extracts, ketaserin, insulin-like growth factor, platelet derived growth factors, epidermal growth factor, interleukin, human alphathrombin, fibroblast growth factors, periodontal ligament chemotactic factor, human growth hormone, animal growth hormone, and growth hormones such as somatotropin. Alternatively or in addition, permeation enhancers, for example, fatty acid esters such as laureate, myristate and stearate monoesters of polyethylene glycol, enamine derivatives, and alpha-keto aldehydes, may be added to the aggregates. An osteoinductive material such as demineralized bone matrix or an osteoconductive material such as a calcium phosphate ceramic may be coated onto a one- or two-dimensional aggregate. An adhesive may be used to adhere the additive to the aggregate if it does not naturally retain itself on the aggregate. Exemplary adhesives include cyanoacrylates, silicones, hot melt adhesives, cellulosic binders, and other adhesives known to those skilled in the art (see, for example, our commonly owned U.S. Pat. No. 5,061,286 to Lyle, the contents of which are incorporated herein by reference).

These materials may be incorporated into the aggregate at any stage of production. For example, they may be combined with a solvent into which tissue particles are mixed, or extruded materials may be passed through a bath containing the biologically active substance. In an alternative embodiment, biologically active substances are added to a single aggregate or to an "aggregate of aggregates," e.g., a gauze woven from aggregates in the form of a thread or strand, a braid or cable, or a multi-plied yarn.

The materials that are incorporated into aggregates may be modified to render them osteoinductive if they are not already. For example, connective tissue may be rendered osteoinductive by association with, or incorporation of, various osteoinductive materials which include, but are not limited to, growth factors such as bone-derived growth factor, bone morphogenic proteins, osteogenic proteins such as OP-1, hormones, growth hormone, platelet derived growth factor (PDGF), insulin-like growth factors (IGF-1)(IGF-2), DNA-encoding various therapeutic agents such as growth factors and hormones, gene activated matrix, i.e., a matrix containing DNA encoding therapeutic proteins utilized to promote cell growth, which in turn, promote DNA transfer into repair cells, demineralized bone in the form of particles, powder, gel, liquid, etc, ceramic powders of calcium phosphate and/or apatite (hydroxyapatite) and bioglasses. Bone morphogenic proteins can be obtained from Genetics Institute, Inc. (Cambridge, Mass.) and Stryker Corporation (Kalamazoo, Mich.) and may also be prepared by one skilled in the art as described, e.g., in. U.S. Pat. Nos. 5,187,076, 5,366,875, 4,877,864, 5,108,922, 5,116,738, 5,013,649, 5,106,748, WO93/00432, WO94/26893 and WO94/26892, each of which is incorporated by reference herein. All osteoinductive factors are contemplated whether they are obtained as above or isolated from bone or other human or animal tissues. Methods for isolating bone morphogenic protein from bone are described, e.g., in U.S. Pat. No. 4,294,753, incorporated herein by reference. Methods of preparing demineralized bone powder, demineralized bone particles, and demineralized bone in the form of a liquid, and demineralized bone in the form of a gel are well known in the art as described, e.g., in U.S. Pat. Nos. 5,314,476, 5,507,813, 5,073,373, and 5,405,390, respectively, each of which is incorporated by reference herein. Methods of preparing osteogenic proteins, such as OP-1 are described, e.g., in U.S. Pat. No. 6,048,964 which is incorporated by reference herein. Methods of transferring DNA-encoding therapeutic proteins into repair cells utilizing gene activated matrix are described, e.g., in U.S. Pat. No. 5,962,427 which is incorporated by reference herein. Methods of preparing ceramic powders of calcium phosphate and/or hydroxyapatite are described, e.g., in U.S. Pat. Nos. 4,202,055 and 4,713,076, each of which is incorporated by reference herein. Methods of preparing bioglasses are described, e.g., in WO 98/44965, which is incorporated by reference herein. Suitable methods of incorporation or association of such osteogenic factors include coating, immersion saturation, packing, spraying, e.g., plasma spraying, injecting into the tissue, etc.

Cells may be seeded onto aggregates or completed implants. In one embodiment, cells may be encapsulated in a matrix such as alginate or collagen gel and the capsules placed on the aggregate or implant. Methods for encapsulating cells are well known to those skilled in the art; an exemplary method is disclosed in U.S. Pat. No. 4,391,909, the contents of which are incorporated herein by reference. Seeded implants do not need to be incubated for long periods of time in solutions that could partially dissolve the binding agent. Instead, the capsules may be placed on the aggregate or implant shortly before implantation. In another embodiment, cells are simply mixed with a gel which is then combined with the aggregate. Alternatively, completed aggregates or implants may be cultured with cells before implantation. In one embodiment, thicker aggregates are used for culturing to increase mechanical integrity during implantation. Any class of cells, including connective tissue cells, organ cells, muscle cells, nerve cells, and stem cells, may be seeded onto the implant. In an exemplary embodiment, connective tissue cells such as osteoblasts, osteoclasts, fibroblasts, tenocytes, chondrocytes, and ligament cells and partially differentiated stem cells such as mesenchymal stem cells and bone marrow stromal cells are employed.

The aggregates may be adapted for use in a variety of tissues and organs. Aggregates may be produced in the form of, for example, a ribbon, gauze, tape, or suture. In one embodiment, sutures or tapes are produced using the aggregates and used to anchor a ligament, tendon, or prosthetic device to bone. As the aggregate is remodeled, it will be incorporated into the bone. In another embodiment, the threads may be used to effect bone-to-bone connections in place of a ligament. Cables may also replace metal cables in applications such as trochanteric osteotomy. Films and cables may replace metal meshes and cables for spinal fusion or attachment of transverse process implants.

Two dimensional aggregates produced according to the invention are ideal for coating irregularly shaped objects. Depending on the application, such aggregates may have large mesh sizes (large holes) or be solid or tightly woven sheets. For example, these aggregates may be used to wrap the femoral step of a hip prosthesis. If a stem is too small to achieve a press fit, or a desired gap between the stem and the drilled hole is too large, the aggregate may be used to increase the width of the stem. In one embodiment, the aggregate may be adjusted introperatively by molding it to fit the reamed canal on one side and the implant on the other side. Indeed, it may be that only certain sections of the stem require bulking. In another embodiment, an aggregate may be used to cover a bony defect that has been filled with a bone substitute material or other osteoinductive or osteoconductive filler. The film prevents the filler from leaking out of the defect.

Two dimensional aggregates may also be used as a substitute for pins in repairing badly fractured bones. Instead of using pins to hold bone fragments together, the set bone pieces may be wrapped with an aggregate. An adhesive may be used to hold it in place. Aggregates may be exploited in a similar fashion for craniofacial reconstruction or plastic surgery. For example, layers of two dimensional aggregates may be used to build up a portion of the jaw or cranial bones or to maintain the surface contours of a filled defect.

In another embodiment, the aggregates may be used to secure dental implants. Two-part dental implants include a metal post or flange that is embedded under the gum with a protruding base that supports an artificial tooth. Food particles and germs from the mouth can penetrate under the gum through the gap between the gum and the post. In healthy teeth, the periodontal ligament provides a barrier between the gingiva and the mouth. An aggregate may be wrapped around the base or deposited directly on thereon. The gum will grow against the implant, sealing the gap.

Two dimensional aggregates may also be used to resurface abraded or damaged bones. For example, aggregates may be used to coat articular surfaces such as the acetabular cup, patella, and talar dome. Injuries to wrist bones such as the hamate and scaphoid may also be treated using the techniques of the invention. The films may also be used to resurface or rejuvenate damaged surfaces resulting from Charcot joints.

In addition, both two and one dimensional aggregates may be used in a wide variety of orthopedic, neurosurgical and oral and maxillofacial surgical procedures such as the repair of simple and compound fractures and non-unions, external and internal fixations, joint reconstructions such as arthrodesis, general arthroplasty, cup arthroplasty of the hip, femoral and humeral head replacement, femoral head surface replacement and total joint replacement, repairs of the vertebral column including spinal fusion and internal fixation, tumor surgery, e.g. deficit filling, discectomy, laminectomy, excision of spinal cord tumors, anterior cervical and thoracic operations, repair of spinal injuries, scoliosis, lordosis and kyphosis treatments, intermaxillary fixation of fractures, mentoplasty, temporomandibular joint replacement, alveolar ridge augmentation and reconstruction, inlay bone grafts, implant placement and revision, sinus lifts, repair of ligaments or tendons in the hand, elbow, knee, foot, ankle or any other anatomical location, etc. These materials can be sutured or stapled in place for anchoring purposes and serve in guided tissue regeneration or as barrier materials.

In another embodiment, aggregates may be formed into a gauze. The gauze may be either woven or non-woven. For example, single threads, extruded polymer-tissue particle composites, or plied yarns may be woven into a gauze. Alternatively or in addition, a precursor material according to the various embodiments discussed above may be cast, pressed, or molded to form a gauze. The gauze may be porous. A porous gauze may be used to retain a small molecule, drug, bioactive agent, or other material by capillary action. For example, a solution containing a BMP or an anti-inflammatory agent may be absorbed into a gauze before implantation.

In another embodiment, the aggregates may be formed into straps having a one-way ratchet. The flexible materials described herein are particularly suited for such an application. The strap may be cut out of a sheet of the aggregate, for example, a cast or pressed two dimensional aggregate, or may be fabricated in the desired shape using the techniques described above. For example, a precursor material may be charged into a shallow mold and the solvent evaporated. Straps may be used to secure other implants around long bones or to reinforce a connection, for example, between two halves of a broken bone. Straps may also be used to provide a suture site at a bone without having to drill a hole through a portion of the bone or to reinforce a suture to bone. Tendon grafts are often implanted with bone at both ends (bone-tendon-bone). Straps produced according to the invention may be exploited to reinforce the union between the implant end and the bone at the implant site.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. An implant comprising a flexible porous gauze woven from a plurality of cohesive aggregate strands, each of the cohesive aggregate strands comprising bone particles and a gene activated matrix, and the bone particles of each strand are retained in a polymer matrix, the polymer matrix having a particle width from about 0.05 mm to about 150 mm.

2. The implant of claim 1, wherein the polymer matrix is or comprises polyurethane.

3. The implant of claim 1, wherein the gauze is woven from the plurality of cohesive aggregate strands in the form of a braid.

4. The implant of claim 1, wherein the polymer matrix is or comprises a polylactide, poly(L-lactide-co-DL-lactide), or tyrosine-based polycarbonate.

5. The implant of claim 1, wherein the porous gauze retains an agent; the agent being selected from the group consisting of trophic factors, adhesives, plasticizers, therapeutic agents, biostatic agents, biocidal agents, bioactive agents, biomolecules, small molecules, and any combinations of the above.

6. The implant of claim 1, wherein the implant further comprises a substrate on which the gauze is coated.

7. The implant of claim 6, wherein the substrate has a shape selected from the group consisting of a member of a bone, sponge, cone, portion of cone, tube, particle, rod, sphere, strand, coiled strand, capillary network, film, fiber, mesh, sheet, threaded cylinder, rod, hinge, rivet, anchor, spheroid, ellipsoid, oblate spheroid, prolate ellipsoid, hyperbolic paraboloid and bulk implant.

8. The implant of claim 1, further comprising cells selected from the group consisting of connective tissue cells, organ cells, muscle cells, nerve cells, and stem cells.

9. The implant of claim 8, wherein the cells are selected from the group consisting of osteoblasts, osteoclasts, tenocytes, fibroblasts, chondrocytes, ligament cells, and mesenchymal stem cells.

10. The implant of claim 1, further comprising a permanent implant about at least a portion of which the gauze is wrapped.

11. The implant of claim 1, wherein the implant is a composite comprising the gauze and a second material, wherein the second material is selected from the group consisting of a hydrogel, a ceramic, a metal, a natural polymer, a synthetic, recombinant, or modified version of a natural polymer, and a synthetic polymer.

* * * * *